United States Patent [19]

Scire

[11] 4,252,113
[45] Feb. 24, 1981

[54] SPLINT BOARD FOR AN INJURED PERSON WEARING A HELMET

[76] Inventor: Lawrence Scire, 1415 Rosement, Chicago, Ill. 60660

[21] Appl. No.: 46,657

[22] Filed: Jun. 8, 1979

[51] Int. Cl.³ .............................................. A61F 5/04
[52] U.S. Cl. ................. 128/134; 128/87 R; 5/82 R; 269/328
[58] Field of Search .................... 128/133, 134, 87 R; 5/82 R; 269/328

[56] References Cited

U.S. PATENT DOCUMENTS

| 3,343,180 | 9/1967 | Lothschuetz | 5/82 |
| 3,461,858 | 8/1969 | Michelson | 5/82 |
| 3,650,523 | 3/1972 | Darby | 128/134 |
| 3,889,668 | 6/1975 | Ochs et al. | 128/134 |
| 4,024,861 | 5/1977 | Vincent | 128/87 R |
| 4,034,748 | 7/1977 | Winner | 128/87 R |

Primary Examiner—John D. Yasko

[57] ABSTRACT

A splint board is provided with a pair of helmet-engaging support members for immobilizing a helmet worn by an injured person and straps for holding the person against the splint board. Each of the helmet-engaging support members is movably mounted on the splint board for movement toward and away from each other whereby the support members can be moved into clamping engagement with opposite sides of the helmet. Each support member can be releasably locked in the desired position on the splint board.

12 Claims, 6 Drawing Figures

4,252,113

SPLINT BOARD FOR AN INJURED PERSON WEARING A HELMET

BACKGROUND AND SUMMARY

This invention relates to a splint board for immobilizing the head and cervical spine of an injured person who is wearing a helmet, and, more particularly, to a splint board which can be used without removing the helmet from the person.

Unfortunately, serious neck and back injuries can be experienced by a person even though he is wearing protective headgear. For example, protective headgear or helmets are usually worn by football and hockey players and other athletes, motorcyclists, automobile racers, snowmobilers, etc. When an accident occurs and the player is injured, the nature or seriousness of the injury often cannot be diagnosed at the site of the accident. Frequently, the injury is aggravated when the person is moved, as when his helmet is removed or when the person is lifted or carried by a stretcher.

The safest procedure is to transport the person to a hospital or emergency treatment facility where the injury can be properly diagnosed and treated. However, if the head and neck of the person are not immobilized before the person is moved, the injury can be aggravated during transport.

A common apparatus for immobilizing a person with a neck or back injury is a splint board to which the person is strapped. Weights and/or skull tongs may also be used to provide traction. However, tongs or other devices which engage the head require the removal of the helmet, and merely removing the helmet might aggravate the injury.

The invention immobilizes an injured person for transport without removing his helmet. The inventive device includes a splint board which is slid beneath the person and to which the person is strapped. The head end of the splint board is provided with a pair of slots on each side, and a pair of helmet-support members are moved toward each other along the slots into clamping engagement with the helmet. When the helmet supports are properly positioned, bolts on the helmet supports which extend through the slots are tightened to clamp the helmet supports in the desired position. An adjustable helmet strap can be attached to the helmet supports for holding the helmet against the splint board, and an adjustable chin strap can be attached to the helmet supports for holding the chin of the person. The helmet is prevented from moving by the helmet-support members, and the usually tight fit between the helmet and the person's head immobilizes the head and neck. The chin strap and helmet strap assist in immobilizing the person.

DESCRIPTION OF THE DRAWING

The invention will be explained in conjunction with an illustrative embodiment shown in the accompanying drawing in which—

DESCRIPTION OF SPECIFIC EMBODIMENT

Figure 1:
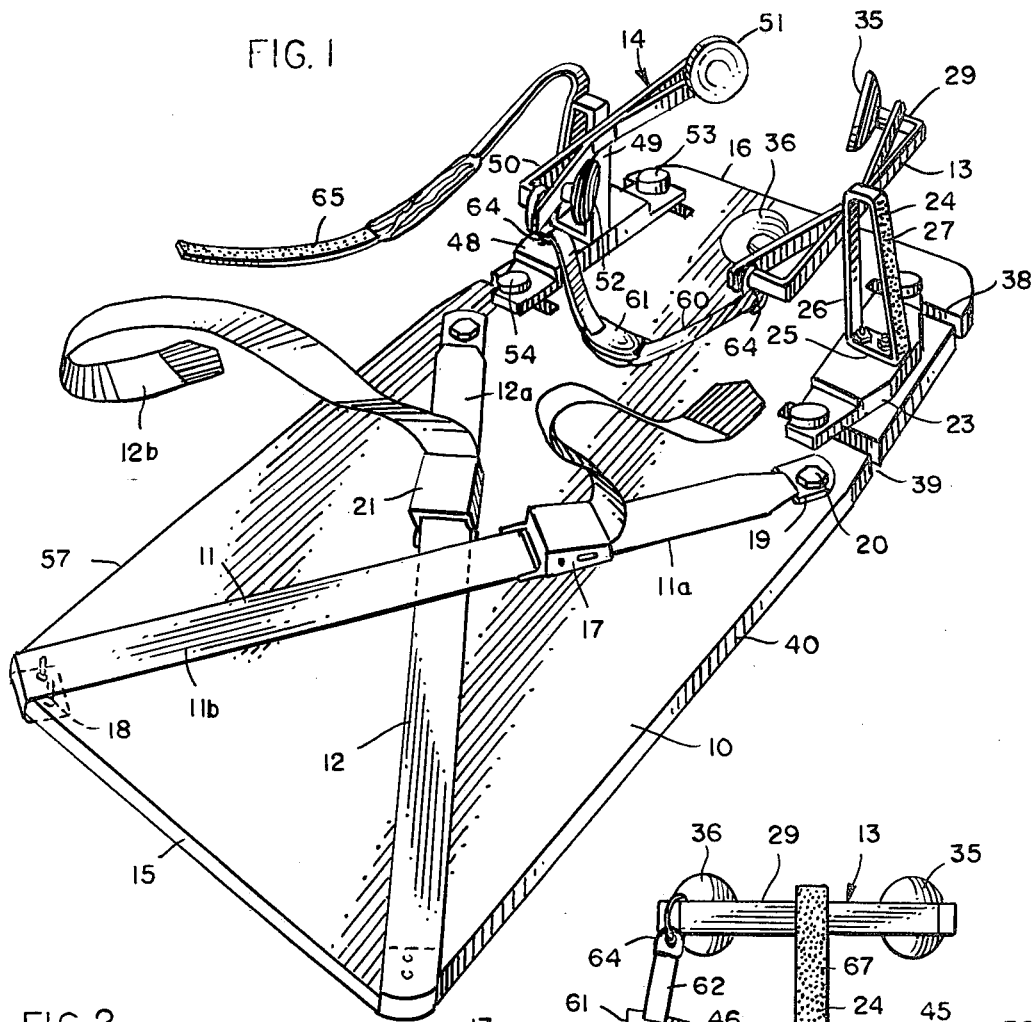
FIG. 1 is a perspective view of a spling board formed in accordance with the invention.
Figure 2:
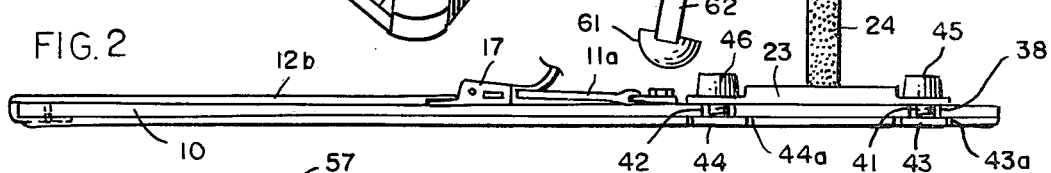
FIG. 2 is a side elevational view of the splint board.
Figure 3:
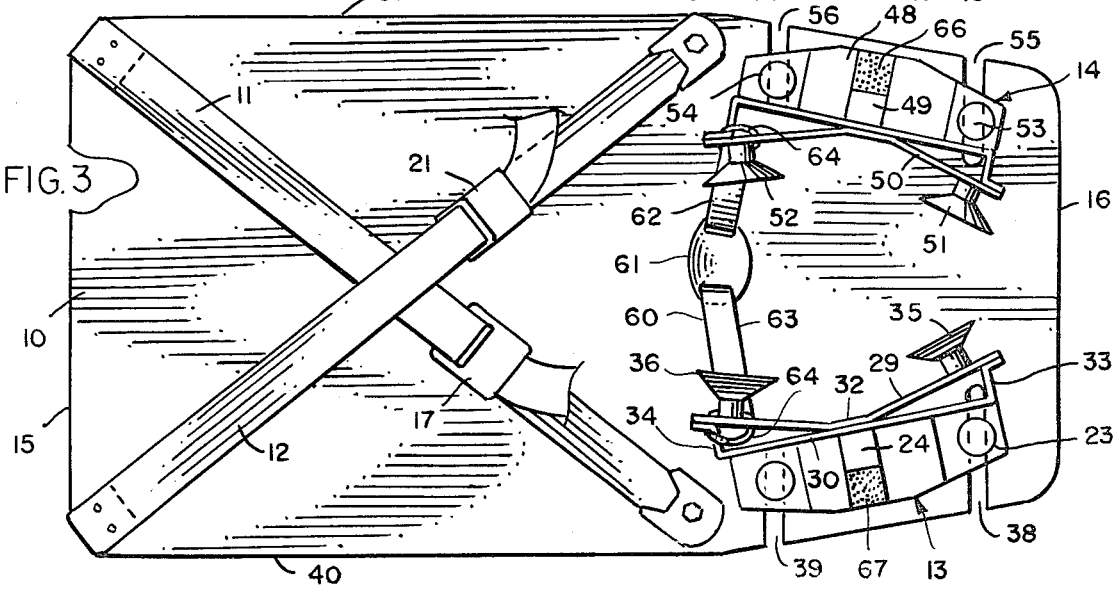
FIG. 3 is a top plan view of the splint board.

Referring first to FIGS. 1–3, an elongated, flat splint board 10 is equipped with a pair of crossing chest straps 11 and 12 and a pair of helmet-support assemblies 13 and 14. The length of the splint board may vary, and the particular splint board illustrated has a length such that the lower end 15 will be located in the lower back area of the victim and the upper or head end 16 will extend beyond the victim's head. The splint board may be formed from any material which will provide the desired strength and rigidity, such as wood or plastic. Although the splint board shown in the drawings is planar, the board may be contoured if desired to conform more closely to the body of the person.

The chest strap 11 includes an upper half 11a and a lower half 11b which are joined by a buckle 17. The strap 11b extends over the lower edge of the splint board and is secured to the lower surface of the splint board by fasteners 18. The strap 11a is secured to the top surface of the splint board by an attaching plate 19 and a bolt 20. The buckle 17 can be a conventional automotive or airplane seatbelt buckle which permits the straps 11a and 11b to be quickly tightened and released.

The strap 12 similarly includes upper and lower strap portions 12a and 12b which are releasably joined by a buckle 21.

The helmet suppoty assembly 13 includes a base plate 23 which is supported by the splint board and an upright or standard 24 which extends upwardly perpendicularly to the splint board. The standard is generally trapeziodally shaped and includes a base portion 25 which is bolted to the base plate 23, a pair of upright portions 26 and 27, and a top portion 28.

A cross member 29 is secured to the upright portion 26 of the standard and extends parallel to the splint board. The cross member and the base plate 23 provide the helmet support assembly with a generally H-shape (FIG. 2). As can be seen best in FIG. 3, the cross member 29 includes an elongated outer straight portion 30 which is secured to the upright portion 26 of the standard, as by welding, and an inner portion 31 which is somewhat V-shaped and which includes a central flat portion 32 which is welded to the outer portion 30. The ends of the outer portion 30 extends inwardly at 33 and 34 and are welded to the ends of the inner portion 29.

A pair of rubber suction cups 35 and 36 are mounted adjacent to the ends of the inner member 31, and the V-shape of the inner member angles the suction cups slightly toward each other.

The splint board is provided with a pair of slots 38 and 39 which extend inwardly from the side edge 40 of the splint board. A pair of bolts 41 and 42 (FIG. 2) extend through the base plate 23 of the helmet assembly and through the slots 38 and 39, respectively. Nuts 43 and 44 which are threadedly engaged with the bolts extend through the sides of the slot and are positioned within wider slots 43a and 44a, respectively, in the bottom surface of the splint board. The flat surfaces of the nuts are engageable with the sides of slots 43a and 44a to prevent the nuts from rotating. However, it is desirable that the slots 38 and 39 and 43a and 44a be slightly wider than the bolts and nuts so that the base plate 23, and therefore the suction cups 35 and 36, can be pivoted somewhat about an axis extending perpendicularly to the splint board. Hand wheels 45 and 46 are secured to the upper ends of the bolts to facilitate rotating the bolts. As will be explained more fully hereinafter, the base plate can be anchored at a desired position along the length of the slots by tightening the bolts on the nuts.

The helmet support assembly 14 is the mirror image of the helmet support assembly 13 and includes a base plate 48, a standard 49, a cross member 50, and suction cups 51 and 52. Hand wheels 53 and 54 are secured to bolts which extend through slots 55 and 56 which extend inwardly from the side edge 57 of the splint board.

A chin strap 60 extends between the two cross members 29 and 50. The chin strap includes a chin cup 61 and a pair of straps 62 and 63. One end of each strap is secured to the chin cup, and the other end is passed through a ring 64 which hangs on the cross member. The strap is then folded on itself, and the facing portions of the straps are releasably secured by Velcro material. A helmet strap 65 is shown in FIG. 1 attached to the standard 49. The strap is releasably attached to the standard by a strip of Velcro material 66 (FIG. 3), and the other end of the strap can be releasably attached to the other standard 24 by a strip of Velcro material 67 (FIGS. 2 and 3).

Figure 4:
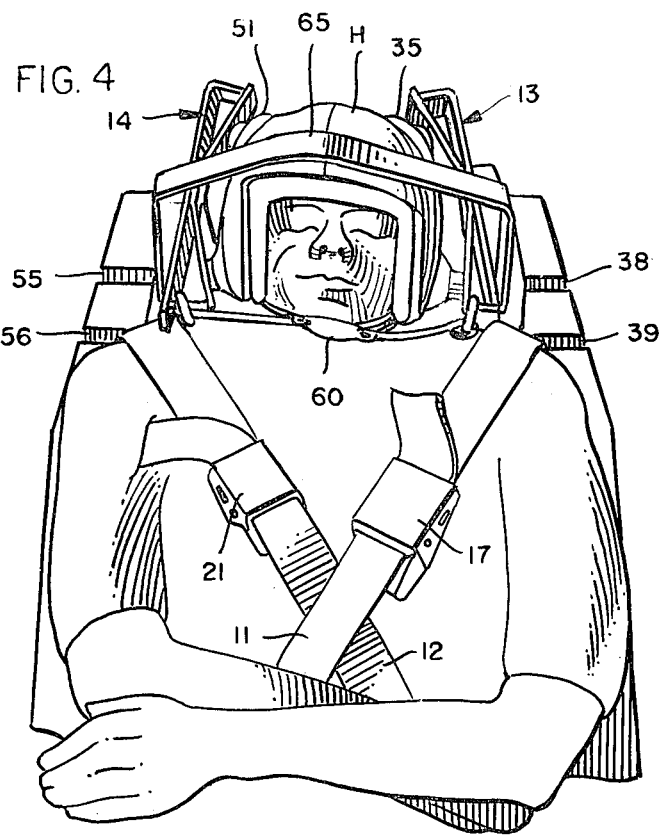
FIG. 4 is a fragmentary front perspective view of an injured football player immobilized by the splint board.
Figure 5:
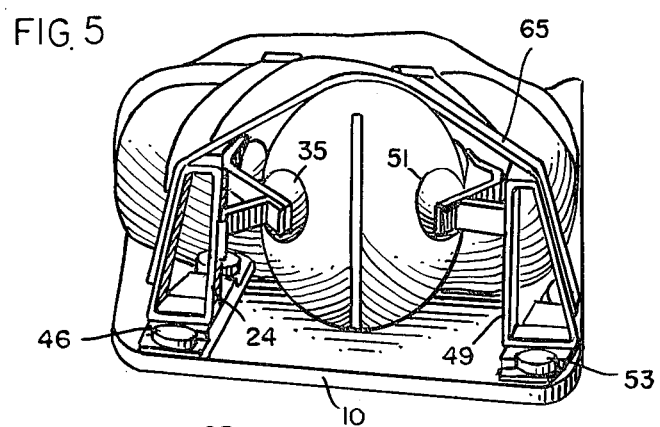
FIG. 5 is a rear fragmentary perspective view of the player and the splint board.
Figure 6:
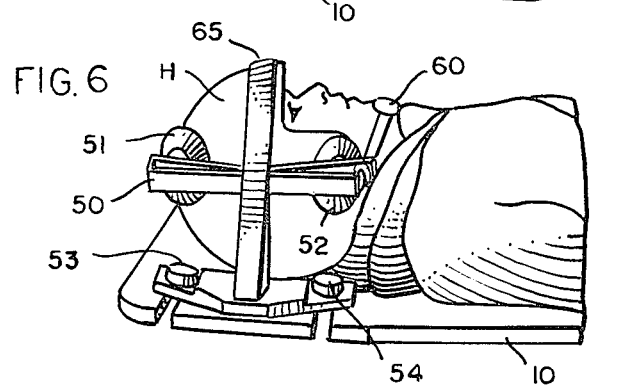
FIG. 6 is a side fragmentary perspective view of the player and the splint board.

FIGS. 4 and 6 illustrate a football player who has suffered a neck or spinal injury. However, it will be understood that the splint board can be used with persons wearing other types of helmets. The splint board is prepared for use by first loosening the bolts which secure the helmet support assemblies and either spreading the helmet support assemblies apart sufficiently to pass over the helmet H worn by the player or entirely removing the helmet support assemblies from the splint board. The slots through which the bolts pass are open-ended to permit the helmet support assemblies to be removed merely by sliding them laterally off of the board. The buckles 17 and 21 are operated to release the chest straps, and the ends of the straps are pulled outwardly away from the splint board.

The splint baord is then slid under the player until the slots in the board are positioned so that the helmet assemblies can be clamped against the helmet. The helmet support assemblies are moved against the helmet until the suction cups 35, 36, 51, and 52 firmly engage the helmet, and the hand wheels of the bolts are then tightened to clamp the base plates immovably against the splint board. The V-shaped members on which the suction cups are mounted permit both suction cups on each side of the helmet to engage the curved surface of the helmet.

The slots in the splint board are preferably wider than the bolts to permit the helmet assemblies to be adjusted slightly in a direction parallel to the head-to-toe direction and to permit the helmet support assemblies to be pivoted slightly about an axis extending perpendicularly to the splint board so that all of the suction cups can be moved into firm engagement with the helmet.

After the helmet support assemblies are clamped in position, the chest straps are tightened over the chest and secured by the buckles. The player is thereby held firmly against the splint board.

Either before or after the chest straps are fastened, the chin straps 60 can be secured to the attaching rings 64 and tightened against the players chin, and the helmet strap 65 can be attached to the standards to ensure that the helmet is held against the splint board. Although the preferred embodiment of the invention includes the chin strap and the helmet strap in order to ensure that the head and cervical spine will be immobilized, the head and cervical can be immobilized by the helmet support assemblies and the chest straps without the chin strap and helmet strap.

After the head and cervical spine are immobilized by the helmet support assemblies and the chest straps, the player can be transported without causing movement which would aggravate the injury. When the player arrives at the hospital, initial treatment can begin even without removing the splint board. When it is desired to remove the splint board, the reverse procedure is followed, and the splint board can be removed quickly and safely without removing the player.

The suction cups will securely anchor the helmet even if they are not attached to the helmet by suction. The suction cups are used primarily because their concave shape is compatible with the contour of the helmet. I have found that the suction cups still completely immobilize the helmet even when they are not attached by suction but merely press against the helmet. On those occasions when the suction cups are attached to the helmet by suction, the helmet is even more secure.

While in the foregoing specification, a detailed description of a specific embodiment of the invention was set forth, it will be understood that many of the details herein given may be varied considerably by those skilled in the art without departing from the spirit and scope of the invention.

I claim:

1. An apparatus for immobilizing the head and spine of a person wearing a helmet comprising splint means for supporting the helmet and the upper back of the person, a pair of helmet supports movably mounted on the splint means for movement toward and away from each other, each of the helmet supports including a pair of helmet-engaging means spaced apart in a direction transverse to the direction of movement of the helmet support for engaging and immobilizing the helmet, and locking means for each of the helmet supports for locking the helmet supports in a position in which the helmet is immobilized by the helmet-engaging means.

2. The apparatus of claim 1 including a helmet strap and means for attaching the helmet strap to each of said helmet supports for holding the helmet against the splint means.

3. The apparatus of claim 1 including adjustable straps attached to the splint means for holding the upper back of the player against the splint means.

4. The apparatus of claim 1 in which the splint means is an elongated, rigid, flat board.

5. An apparatus for immobilizing the head and spine of a person wearing a helmet comprising splint means for supporting the helmet and the upper back of the person, a pair of helmet supports movably mounted on the splint means for movement toward and away from each other, each of the helmet supports including a pair of helmet-engaging means including at least one suction cup for engaging and immobilizing the helmet, and locking means for each of the helmet supports for locking the helmet supports in a position in which the helmet is immobilized by the helmet-engaging means.

6. An apparatus for immobilizing the head and spine of an injured person wearing a helmet comprising splint means for supporting the helmet and the upper back of the person, a pair of helmet supports movably mounted on the splint means for movement toward and away from each other, each of the helmet supports including a base plate movably mounted on the splint means, a standard extending from the base plate generally perpendicular to the splint means, and a cross member attached to the standard and extending generally parallel to the splint means, a pair of helmet-engaging means mounted on each standard at spaced-apart locations for engaging and immobilizing the helmet, and locking means for each of the helmet supports for locking the helmet supports in a position in which the helmet is immobilized by the helmet-engaging means.

7. The apparatus of claim 6 in which each of said helmet-engaging means on each of said cross members comprises a suction cup.

8. The apparatus of claim 6 including a chin strap attached to each of said cross members for engaging the chin of the player.

9. The apparatus of claim 6 in which the locking means for each of said helmet supports includes a bolt extending through the base plate of the helmet support and the splint means and a nut threadedly engaged with the bolt for clamping the base plate against the splint means.

10. The apparatus of claim 6 in which the splint means is provided with a pair of generally parallel elongated slots below each of said base plates, the locking means for each of said helmet supports including a pair of bolts extending through the base plate of the helmet support and through the slots in the splint means and a nut threadedly engaged with each bolt for clamping the base plate against the splint means.

11. The apparatus of claim 10 in which each of said slots has an open end whereby the helmet supports can be removed from the splint means by loosening the nuts and moving the bolts toward the open ends of the slots.

12. The apparatus of claim 6 including a helmet strap and means for attaching the helmet strap to each of said cross members for holding the helmet against the splint means.

* * * * *